United States Patent [19]

Bettarini et al.

[11] Patent Number: 5,541,214

[45] Date of Patent: Jul. 30, 1996

[54] N-POLYHALOBENZYL-PYRAZOLE CARBOXAMIDES ENDOWED WITH ACARICIDAL AND INSECTICIDAL ACTIVITY

[75] Inventors: Franco Bettarini, Novara; Giovanni Meazza, Saronno; Piero La Porta, Novara; Giampaolo Zanardi, Vigevano; Sergio Massimini, Bollate; Franca Reggiori, Novara, all of Italy

[73] Assignee: Isagro S.p.A., Milan, Italy

[21] Appl. No.: 273,826

[22] Filed: Jul. 12, 1994

[30]     Foreign Application Priority Data

Jul. 15, 1993 [IT] Italy ................... MI93A1565

[51] Int. Cl.$^6$ .................. A01N 43/56; C07D 231/14; C07D 231/18; C07D 231/56
[52] U.S. Cl. ............. 514/406; 514/407; 548/363.1; 548/361.5; 548/362.5; 548/369.7; 548/374.1; 548/360.1
[58] Field of Search ............... 548/361.5, 362.5, 548/369.7, 374.1; 514/406, 407

[56]           References Cited

PUBLICATIONS

Chemical Abstracts vol. 113: 115299y (1990).
Chemical Abstracts vol. 116: 6557x (1992).

*Primary Examiner*—Johann Richter
*Assistant Examiner*—Laura R. Cross
*Attorney, Agent, or Firm*—George P. Hoare, Jr.; Rogers & Wells

[57]            ABSTRACT

Amides of pyrazolecarboxy acids having the general formula (I):

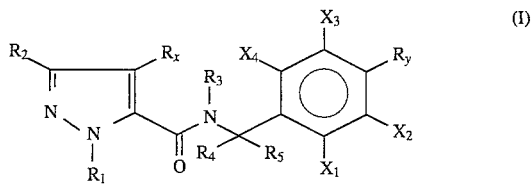

exhibiting a high insecticidal and acaricidal activity.

18 Claims, No Drawings

N-POLYHALOBENZYL-PYRAZOLE CARBOXAMIDES ENDOWED WITH ACARICIDAL AND INSECTICIDAL ACTIVITY

The present invention relates to novel amides of pyrazole carboxy acids,

More particularly, the present invention relates to amides of pyrazole carboxy acids displaying a high acaricidal and insecticidal activity, a process for preparing them, and their use for controlling harmful mites and insects in agricultural, civil and zootechnic fields.

Amides of pyrazole carboxy acids displaying acaricidal and insecticidal activity are already known from European patent application Nos. 289,879; 307,801; 329,020; 365,925; 405,808; 462,573; 521,409. However, the compounds disclosed in the above patent applications display only a secondary insecticidal activity.

The present Applicant has now found that if the amidic nitrogen atom is replaced by a poly-halogenated benzyl group, compounds are obtained which display a surprisingly high acaricidal and insecticidal activity, higher than that displayed by the corresponding N-benzyl pyrazole carboxamides known from the prior art.

Therefore, the present invention provides amides of pyrazole carboxy acids having the general formula (I):

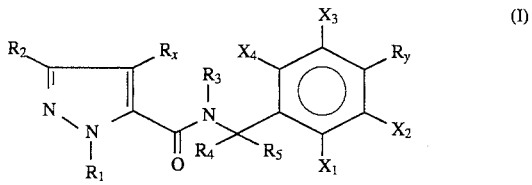

wherein:

$R_1$ and $R_2$ represent, each independently, a linear or branched $C_1$–$C_4$ alkyl radical;

$R_x$ represents a hydrogen atom, a halogen atom, a linear or branched $C_1$–$C_4$ alkyl or haloalkyl radical, a $C_1$–$C_2$ alkoxy or haloalkoxy radical; or when $R_2$ and $R_x$ are taken jointly, they represent a moiety

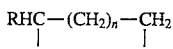

in which R represents a hydrogen atom or a $C_1$–$C_3$ alkyl radical and n is a number between 1 and 2;

$R_3$, $R_4$ and $R_5$ represent, each independently, a hydrogen atom or a linear or branched $C_1$–$C_4$ alkyl radical;

$X_1$, $X_2$, $X_3$ and $X_4$ represent, each independently, a halogen atom; or, when at least two from $X_1$ to $X_4$ represent halogen atoms, a hydrogen atom;

$R_y$ represents a halogen atom, a linear or branched $C_1$–$C_8$ alkyl or haloalkyl radical, a linear or branched $C_1$–$C_8$ alkoxy or haloalkoxy radical, a linear or branched $C_3$–$C_8$ alkoxy alkoxy radical, a $C_3$–$C_8$ cycloalkoxy radical, a $C_4$–$C_8$ cycloalkylalkoxy radical, a $C_1$–$C_8$ alkylthio radical, a trimethylsilyl radical; a linear or branched $C_3$–$C_8$ alkoxyalkyl or haloalkoxyalkyl radical; a $C_2$–$C_8$ alkylamino or dialkylamino radical; or when all of $X_1$–$X_4$ are halogen atoms, $R_y$ represents a phenoxy or a phenylthio radical, with said radicals being optionally substituted with halogen atoms, linear or branched alkyl or haloalkyl $C_1$–$C_4$ radicals, linear or branched $C_1$–$C_4$ alkoxy or haloalkoxy radicals.

The compounds of general formula (I) exhibit high insecticidal and acaricidal activity.

Preferred compounds of general formula (I) according to the present invention are those in which $X_1$, $X_2$, $X_3$ and $X_4$ represent a fluorine atom, with the other substituents having the meanings disclosed hereinabove.

Examples of compounds of general formula (I) which exhibit insecticidal and acaricidal activity are:

N-(4-methyl-2,3,5,6-tetrafluorobenzyl)-4-chloro-3-ethyl-1-methylpyrazole-5-carboxamide;

N-(4-n-propyl-2,3,5,6-tetrafluorobenzyl)-4-chloro-3-ethyl-1-methylpyrazole-5-carboxamide;

N-(4-n-propyl-2,3,5,6-tetrafluorobenzyl)-4-chloro-1,3-dimethylpyrazole-5-carboxamide;

N-(4-n-butyl-2,3,5,6-tetrafluorobenzyl)-4-chloro-3-ethyl-1-methylpyrazole-5-carboxamide;

N-(4-n-butyl-2,3,5,6-tetrafluorobenzyl)-4-chloro-1,3-dimethylpyrazole-5-carboxamide;

N-(4-n-butyl-2,3,5,6-tetrafluorobenzyl)-2,6-dimethyl-2,4,5,6-tetrahydrocyclopentapyrazole-3-carboxamide;

N-(4-isobutyl-2,3,5,6-tetrafluorobenzyl)-4-chloro-3-ethyl-1-methylpyrazole-5-carboxamide;

N-(4-isobutyl-2,3,5,6-tetrafluorobenzyl)-4-chloro-1,3-dimethylpyrazole-5-carboxamide;

N-(4-tert.-butyl-2,3,5,6-tetrafluorobenzyl)-4-chloro-3-ethyl-1-methylpyrazole-5-carboxamide;

N-(4-tert.butyl-2,3,5,6-tetrafluorobenzyl)-4-chloro-1,3-dimethylpyrazole-5-carboxamide;

N-(4-tert.butyl-2,3,5,6-tetrafluorobenzyl)-2,6-dimethyl-2,4,5,6-tetrahydrocyclopentapyrazole-3-carboxamide;

N-[4-(2,2-dimethylpropyl)-2,3,5,6-tetrafluorobenzyl]-4-chloro-3-ethyl-1-methylpyrazole-5-carboxamide;

N-[4-(2,2-dimethylpropyl)-2,3,5,6-tetrafluorobenzyl]-4-chloro-1,3-dimethylpyrazole-5-carboxamide;

N-[4-(2,2-dimethylpropyl)-2,3,5,6-tetrafluorobenzyl]-2,6-dimethyl-2,4,5,6-tetrahydrocyclopentapyrazole-3-carboxamide;

N-(4-n-pentyl-2,3,5,6-tetrafluorobenzyl)-4-chloro-3-ethyl-1-methylpyrazole-5-carboxamide;

N-(4-n-pentyl-2,3,5,6-tetrafluorobenzyl)-4-chloro-1,3-dimethylpyrazole-5-carboxamide;

N-(4-n-pentyl-2,3,5,6-tetrafluorobenzyl)-2,6-dimethyl-2,4,5,6-tetrahydrocyclopentapyrazole-3-carboxamide;

N-[4-(3-methylbutyl)-2,3,5,6-tetrafluorobenzyl]-4-chloro-3-ethyl-1-methylpyrazole-5-carboxamide;

N-[4-(3-methylbutyl)-2,3,5,6-tetrafluorobenzyl]-4-chloro-1,3-dimethylpyrazole-5-carboxamide;

N-[4-(3-methylbutyl)-2,3,5,6-tetrafluorobenzyl]-2,6-dimethyl-2,4,5,6-tetrahydrocyclopentapyrazole-3-carboxamide;

N-(4-n-propoxy-2,3,5,6-tetrafluorobenzyl)-4-chloro-3-ethyl-1-methylpyrazole-5-carboxamide;

N-(4-n-propoxy-2,3,5,6-tetrafluorobenzyl)-4-chloro-1,3-dimethylpyrazole-5-carboxamide;

N-(4-isopropoxy-2,3,5,6-tetrafluorobenzyl)-4-chloro-3-ethyl-1-methylpyrazole-5-carboxamide;

N-(4-isopropoxy-2,3,5,6-tetrafluorobenzyl)-4-chloro-1,3-dimethylpyrazole-5-carboxamide;

N-(4-n-butoxy-2,3,5,6-tetrafluorobenzyl)-4-chloro-3-ethyl-1-methylpyrazole-5-carboxamide;

N-(4-n-butoxy-2,3,5,6-tetrafluorobenzyl)-4-chloro-1,3-dimethylpyrazole-5-carboxamide;

N-(4-n-butoxy-3,5-dichlorobenzyl)-4-chloro-3-ethyl-1-methylpyrazole-5-carboxamide;

N-(4-isobutoxy-2,3,5,6-tetrafluorobenzyl)-4-chloro-3-ethyl-1-methylpyrazole-5-carboxamide;

N-(4-isobutoxy-2,3,5,6-tetrafluorobenzyl)-4-chloro-1,3-dimethylpyrazole-5-carboxamide;

N-(4-isobutoxy-3,5-dichlorobenzyl)-4-chloro-3-ethyl-1-methylpyrazole-5-carboxamide;

N-(4-sec.butoxy-2,3,5,6-tetrafluorobenzyl)-4-chloro-3
-ethyl-1-methylpyrazole-5-carboxamide;
N-(4-sec.butoxy-2,3,5,6-tetrafluorobenzyl)-4-chloro-1,3-
dimethylpyrazole-5-carboxamide;
N-[4-(2,2-dimethylpropoxy)-2,3,5,6-tetrafluorobenzyl]-4-
chloro-3-ethyl-1-methylpyrazole-5-carboxamide;
N-[4-(2,2,-dimethylpropoxy)-2,3,5,6 -tetrafluorobenzyl]-4-
chloro-1,3-dimethylpyrazole-5-carboxamide;
N-[4-(3-methylbutoxy)-2,3,5,6-tetrafluorobenzyl]-4
-chloro-3-ethyl-1-methylpyrazole-5-carboxamide;
N-[4-(3-methylbutoxy)-2,3,5,6-tetrafluorobenzyl]-4
-chloro-1,3-dimethylpyrazole-5-carboxamide;
N-[4-(3-methylbutoxy)-3,5-dichlorobenzyl]-4-chloro-3
-ethyl-1-methylpyrazole-5-carboxamide;
N-(4-cyclopentoxy-2,3,5,6-tetrafluorobenzyl)-4-chloro-3-
ethyl-1-methylpyrazole-5-carboxamide;
N-(4-cyclopentoxy-2,3,5,6-tetrafluorobenzyl)-4-chloro-1,3-
dimethylpyrazole-5-carboxamide;
N-(4-cyclopropylmethoxy-2,3,5,6-tetrafluorobenzyl)-4
-chloro-3-ethyl-1-methylpyrazole-5-carboxamide;
N-(4-cyclopropylmethoxy-2,3,5,6-tetrafluorobenzyl)-4
-chloro-1,3-dimethylpyrazole-5-carboxamide;
N-[4-(2,2,2-trifluoroethoxy)-2,3,5,6 -tetrafluorobenzyl]-4-
chloro-3-ethyl-1-methylpyrazole-5-carboxamide;
N-[4-(2,2,2-trifluoroethoxy-2,3,5,6 -tetrafluorobenzyl]-4-
chloro-1,3-dimethylpyrazole-5 -carboxamide;
N-[4-(2,2,3,3-tetrafluoropropoxy)-2,3,5,6 -tetrafluoroben-
zyl]-4-chloro-3-ethyl-1-methylpyrazole-5-carboxamide;
N-[4-(2,2,3,3-tetrafluoropropoxy)-2,3,5,6 -tetrafluoroben-
zyl]-4-chloro-1,3-dimethylpyrazole-5 -carboxamide;
N-[4-(2,2,3,3,4,4,5,5-octafluoropentoxy)-2,3,5,6 -tetrafluo-
robenzyl]-4-chloro-3-ethyl-1-methylpyrazole-5-carboxa-
mide;
N-[4-(2,2,3,3,4,4,5,5-octafluoropentoxy)-2,3,5,6 -tetrafluo-
robenzyl]-4-chloro-1,3-dimethylpyrazole-5 -carboxam-
ide;
N-(4-n-butylthio-2,3,5,6-tetrafluorobenzyl)-4-chloro-3-
ethyl-1-methylpyrazole-5-carboxamide;
N-(4-n-butylthio-2,3,5,6-tetrafluorobenzyl)-4-chloro-1,3-
dimethylpyrazole-5-carboxamide;
N-(2,3,5,6-tertrafluoro-4-trimethylsilylbenzyl)-4-chloro-3
-ethyl-1-methylpyrazole-5-carboxamide.

The present invention also provides a process for preparing the compounds of general formula (I).

The compounds of general formula (I) can be obtained by means of a process which comprises reacting a derivative of a pyrazole-carboxy acid having the general formula (II)

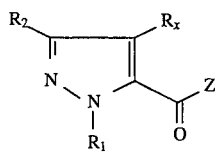

(II)

wherein $R_1$, $R_2$ and $R_x$ have the same meaning as disclosed above, Z represents a halogen atom, such as chlorine or bromine, a hydroxy radical or a linear or branched $C_1$–$C_4$ alkoxy radical, with a benzylamine of general formula (III):

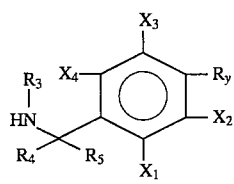

(III)

wherein $R_3$, $R_4$, $R_5$, $X_1$, $X_2$, $X_3$, $X_4$ and $R_y$ have the same meaning as disclosed above.

The reaction can be carried out in the presence or absence of a base and in the presence or absence of a solvent.

In the case where Z represents a chlorine or bromine atom, the reaction is preferably carried out in the presence of an organic or inorganic base and in the presence of a solvent, at a temperature within the range of from 0° C. to the boiling temperature of the reaction mixture (the solvent plus the base and both above disclosed reactants).

Examples of organic bases useful for carrying out the above process are triethylamine, pyridine, N,N-dimethylaminopyridine, etc.

Examples of inorganic bases are sodium hydroxide, potassium hydroxide, sodium carbonate, potassium carbonate, etc.

Examples of solvents useful for carrying out the process disclosed above are benzene, toluene xylene, acetone, methyl ethyl ketone, chloroform, methylene chloride, ethyl acetate, ethyl ether, tetrahydrofuran, dioxane, acetonitrile, N,N-dimethylformamide, N-methylpyrrolidone, dimethyl sulfoxide, water etc.

In the case where Z represents a hydroxy or alkoxy radical, the reaction is preferably carried out in the absence of any bases. In that case, the reaction can be carried out either in the absence or in the presence of a high-boiling solvent such as N,N-dimethylformamide, N-methylpyrrolidone, dimethyl sulfoxide, etc., at a temperature within the range of from 150° C. to 250° C., The derivatives of pyrazole carboxy acid of general formula (II) are known from technical literature and can be prepared for example according to that reported in "Bulletin de la Societé Chimie de France", 1966, p. 293; in "Farmaco Ed. Sc.", Vol. 22, 1967, p. 692 and in "Annalen der Chemie", Vol 598, 1956, p. 186.

The benzylamines of general formula (III) can be prepared according to well known methods of practical organic synthesis, such as described for example in "Beilstein Handbuch der Organischen Chemie", Vol 12, Chapter III, p. 2343.

The compounds of general formula (I) according to the present invention display a high level of acaricidal and insecticidal activity against insect and mite adults, larvae and their eggs dangerous in agricultural, civil and zootechnic fields.

In particular, the compounds of general formula (I) are active against important species of Coleoptera (*Leptinotarsa decemlineata, Callosobruchus chinensis*, and so forth), Hemyptera (*Macrosiphum euphorbiae, Myzus persicae, Psylla pyricola*, and so forth), Diptera (*Aedes Aegypti, Musca domestica*, and so forth), Lepidoptera (*Spodoptera littoralis, Chilo suppressalis*, and so forth), and several families of mites, e.g., Tetranychus spp. (*Tetranychus urticae, Tetranychus telarius, Panonychus ulmi, Panonychus citri*, and so forth), Eryophes spp. (*Phytoptus avellanae, Eryophes vitis, Erophyes pyricola*, and so forth; Tarsonemidae *Steneotarsonemus pallidus*, and so forth).

At the same time, the compounds of general formula (I) display a low level of toxicity for a large number of useful insects and mites, mammals, fishs, amphibia and birds and do not exhibit phytotoxicity.

Due to their positive characteristics, the compounds of general formula (I) can be advantageously used to defend from insect and mite pests in crops of agricultural and horticultural interest, and domestic animals and husbandry livestock, as well as sites frequented by humans.

For practical use in agricultural and in other fields, it is often advantageous to use compositions of insecticidal and acaricidal activity containing one or more compounds of general formula (I) as active substance.

Compositions can be used which are in the form of dry dusts, wettable powders, emulsifiable concentrates, microemulsions, pastes, granular formulations, solutions, suspensions etc. The selection of formulation type will depend on the contemplated specific use.

The compositions are prepared according to well known methodologies, for example by diluting or dissolving the active substance with a solvent and/or a solid diluent, possibly in the presence of surfactants.

Suitable solid inert diluents or carriers include China clay, alumina, silica, talc, bentonite, chalk, quartz, dolomite, attapulgite, montmorillonite, diatomaceous earth, cellulose, starch, etc.

Suitable liquid inert diluents include, in addition to water, organic solvents such as aromatic hydrocarbons (xylenes, blends of alkylbenzenes, and so forth), or aliphatic hydrocarbons (hexane, cyclohexane, and so forth), as well as halogenated aromatic hydrocarbons (chlorobenzene, and so forth), alcohols (methanol, propanol, butanol, octanol, and so forth), esters (isobutyl acetate, and so forth), ketones (acetone, cyclohexanone, acetophenone, isoforone, ethyl amyl ketone, and so forth), or vegetable or mineral oils, or mixtures thereof, etc.

Suitable surfactants include wetting agents and emulsifiers of non-ionic type (polyethoxylated alkyl phenols, polyethoxylated fatty alcohols, etc.), anionic type (alkylbenzene sulfonates, alkyl sulfonates, etc.) and cationic types (quaternary alkylammonium salts, etc.)

Furthermore, dispersants (e.g., lignine and its salts, cellulose derivatives, alginates, etc.) and stabilizers (e.g., antioxidants, U.V. light absorbants, etc.), can be added.

In order to extend the active range of the above said compositions, additional active agents can be added such as other insecticides or acaricides, herbicides, fungitides, fertilizers.

The concentration of active substance in the above said compositions may vary within a wide range according to the active compound, the applications they are destined to, the environmental conditions, and the type of formulation adopted.

In general, the concentration of active substance is within the range of from 1% to 90%, preferably of from 5% to 40%.

Also the application rates vary depending on several factors such as the type of pest and the degree of infestation, the type of composition used, and climatical and environmental factors.

For practical uses in agriculture, active compound application rates within the range of from 10 g to 500 g per hectare provide a sufficient protection.

The following examples are reported for illustrative purposes and do not limit the present invention.

In the spectra of protonic nuclear magnetic resonance ($^1$H-NMR) reported in the following examples, the following abbreviations were used:

s=singlet; d=doublet; t=triplet; q=quartet; tt=triplet of triplets; bt=broad triplet; m=multiplet, or complex signal.

EXAMPLE 1

Preparation of intermediate polyhalo-benzylamines

The benzylamines used in order to prepare the compounds displayed in the following examples were obtained by starting from the corresponding benzyl halides by means of a Gabriel synthesis ("A" method), or from the corresponding benzonitriles by catalytic hydrogenation, e.g., according to that procedure disclosed in U.S. Pat. No. 4,965,394, or by chemical reduction ("B" method).

"A" METHOD

Preparation of
4-n-butyl-2,3,5,6-tetrafluorobenzylamine

A mixture consisting of 2,8 g (11 mmol) of 4-n-butyl-2, 3,5,6-tetrafluorobenzyl chloride (obtained from the corresponding alcohol, prepared in its turn, according to a similar procedure to as disclosed in U.S. Pat. No. 4,405,640), 2,1 g (11.5 mmol) of potassium phthalimide and 50 ml of dimethyl formamide is heated at 50° C. for 1 hour. After cooling, the reaction mixture is poured into 200 ml of 2% aqueous sodium hydroxide and is extracted with ethyl ether (3×50 ml). The organic phase is washed with water (50 ml) and saturated sodium chloride solution (50 ml), thoroughly dried with sodium sulfate, and concentrated.

2.9 g of solid residue is obtained, which is suspended in 15 ml of ethanol at 95%. 450 mg (9 mmol) of hydrazine hydrate is added and the mixture is refluxed for 2 hours. The solvent is evaporated off and the residue is collected with water (100 ml) and extracted with ethyl ether (3×30 ml). The organic phase is washed with water (50 ml) and saturated sodium chloride solution (50 ml), thoroughly dried over sodium sulfate and evaporated. 1.65 g of a yellow oil is obtained which is used without any further purification in order to prepare Compound Nos. 1 and 2.

$^1$H-NMR (CDCl$_3$): δ at 0.9 (t, 3H); 1.25–1.65 (m, 6H); 2.7 (t, 2H); 3.95 (s, 2H).

"B" METHOD

Preparation of
4-isobutoxy-2,3,5,6-tetrafluorobenzylamine

A solution of 2.07 g of aluminum chloride (15.3 mmol) in anhydrous ethyl ether (25 ml) is dropwise added to a suspension of 590 mg (15.3 mmol) of lithium aluminum hydride in anhydrous ethyl ether (15 ml). The solution is kept with stirring at room temperature for 15 minutes.

A solution of 3.77 g (15.3 mmol) of 4-isobutoxy-2,3,5, 6-tetrafluorobenzonitrile (prepared by means of a similar procedure to that reported in Journal Chemical Society (C), 1971, p. 1343–1348) in anhydrous ethyl ether (25 ml), is added very slowly to the above mixture. The resulting mixture is kept under stirring at room temperature for 2 hours. 5 ml of water is carefully added, the mixture is then poured into 100 ml of aqueous 10% sodium hydroxide. The mixture is extracted with ethyl ether (3×50 ml). The combined organic phase is then treated with hydrochloric acid at 20% (50 ml). The acidic liquors are then alkalified with aqueous sodium hydroxide at 50%, and extracted with ethyl ether (3×50 ml). The ethereal phase is washed with water (50 ml), thoroughly dried with sodium sulfate, and concentrated. 3.3 g of amine is obtained, which is used to prepare Compound No. 15.

$^1$H-NMR (CDCl$_3$): δ at 0.95 (d, 6H); 1.6 (bs, 2H); 2.05 (m, 1H); 3.95 (d, 2H); 4.0 (s, 2H).

By using one of the above methods, the following were obtained:
4-n-pentyl-2,3,5,6-tetrafluorobenzylamine;
4-iso-propoxy-2,3,5,6-tetrafluorobenzylamine;
4-n-butoxy-2,3,5,6-tetrafluorobenzylamine;
4-cyclopentoxy-2,3,5,6-tetrafluorobenzylamine;
4-(2,2,2-trifluoroethoxy)-2,3,5,6 -tetrafluorobenzylamine;
4-(2,2,3,3-tetrafluoropropoxy)-2,3,5,6 -tetrafluorobenzylamine;

4-(2,2,3,3,4,4,5,5-octafluoropentoxy)-2,3,5,6 -tetrafluorobenzylamine;
4-(3-methylbutoxy)-2,3,5,6-tetrafluorobenzylamine;
4-n-butylthio-2,3,5,6-tetrafluorobenzylamine;
4-n-pentylthio-2,3,5,6-tetrafluorobenzylamine;
4-(3-methylbutylthio)-2,3,5,6-tetrafluorobenzylamine;
4-(3-methylbutyl)-2,3,5,6-tetrafluorobenzylamine;
4-tert.-butyl-2,3,5,6-tetrafluorobenzylamine;
4-n-pentoxy-2,3,5,6-tetrafluorobenzylamine;
4-(4-methylpentoxy)-2,3,5,6-tetrafluorobenzylamine;
4-(4-methylpentyl)-2,3,5,6-tetrafluorobenzylamine;
4-(3,3-dimethylbutoxy)-2,3,5,6-tetrafluorobenzylamine;
4-(N'-methyl-n-butylamino)-2,3,5,6 -tetrafluorobenzylamine;
4-(N'-methyl-n-pentylamino)-2,3,5,6 -tetrafluorobenzylamine;
4-n-pentylamino-2,3,5,6-tetrafluorobenzylamine;
4-isobutoxymethyl-2,3,5,6-tetrafluorobenzylamine;
4-(3-methylbutoxy)-3,5-dichlorobenzylamine;
4-(4-methylpentoxy)-3,5-dichlorobenzylamine;
4-(3,3-dimethylbutoxy)-3,5-dichlorobenzylamine.

EXAMPLE 2

Preparation of N-(4-n-butyl-2,3,5,6 -tetrafluorobenzyl)-4-chloro-3-ethyl-1 -methylpyrazole-5-carboxamide. (Compound No. 1)

A mixture consisting of 10 ml of methylene chloride, 0.45 ml of triethylamine and 680 mg (2.9 mmol) of 4-n-butyl-2,3,5,6-tetrafluorobenzylamine is slowly added dropwise to a solution of 600 mg (2.9 mmol) of 4-chloro-3-ethyl-1-methyl-5-pyrazole carboxy acid chloride in 5 ml of methylene chloride.

The reaction mixture is kept under stirring at room temperature for 6 hours.

After removing the solvent from the rotary evaporator, to the residue, 100 ml of a 1% solution of hydrochloric acid is added. The resulting mixture is then extracted with ethyl ether (3×70 ml).

The resulting organic phase is washed with a saturated sodium hydrogencarbonate solution (20 ml), thoroughly dried with sodium sulfate and concentrated on the rotary evaporator.

The resulting crude material (1.2 g) is purified by silica gel chromatography, eluting with 85:15 hexane:ethyl acetate.

990 mg of the reaction product (Compound No. 1) is obtained, which, after crystallization from hexane, has a melting point (m.p.) of 87°–90° C.

$^1$H-NMR (CDCl$_3$): δ at 0.9 (t, 3H); 1.2 (t, 3H); 1.25–1.65 (m, 4H); 2.6 (q, 2H); 2.7 (t, 2H); 4.1 (s, 3H); 4.7 (d, 2H); 7.2 (bt, 1H).

EXAMPLE 3

By operating analogously to the procedure as disclosed in Example 1, the following compounds were prepared.

N-(4-n-butyl-2,3,5,6-tetrafluorobenzyl)-4-chloro-1,3-dimethylpyrazole-5-carboxamide (Compound No. 2) with m.p. 89°–90° C.

$^1$H-NMR (CDCl$_3$): δ at 0.9 (t, 3H); 1.25–1.65 (m, 4H); 2.2 (s, 3H); 2.7 (t, 2H); 4.1 (s, 3H); 4.7 (d, 2H); 7.2 (bt, 1H).

N-(4-n-pentyl-2,3,5,6-tetrafluorobenzyl)-4 -chloro-3-ethyl-1-methylpyrazole-5-carboxamide (Compound No. 3) with m.p. 87°–88° C.

$^1$H-NMR (CDCl$_3$): δ at 0.95 (t, 3H); 1.2 (t, 3H); 1.25–1.7 (m, 6H); 2.6 (q, 2H); 2.7 (t, 2H); 4.1 (s, 3H); 4.7 (d, 2H); 7.2 (bt, 1H).

N-(4-n-pentyl-2,3,5,6-tetrafluorobenzyl)-4 -chloro-1,3-dimethylpyrazole-5-carboxamide (Compound No. 4) with m.p. 83°–84° C.

$^1$H-NMR (CDCl$_3$): δ at 0.95 (t, 3H); 1.25–1.7 (m, 6H); 2.2 (s, 3H); 2.7 (t, 2H); 4.1 (s, 3H); 4.7 (d, 2H); 7.2 (bt, 1H).

N-(4-isopropoxy-2,3,5,6-tetrafluorobenzyl)-4 -chloro-3-ethyl-1-methylpyrazole-5-carboxamide (Compound No. 5) with m.p. 92°–93° C.

$^1$H-NMR (CDCl$_3$): δ at 1.2 (t, 3H); 1.35 (d, 6H); 2.6 (q, 2H); 4.1 (s, 3H); 4.55 (m, 1H); 4.7 (d, 2H); 7.2 (bt, 1H).

N-(4-n-butoxy-2,3,5,6-tetrafluorobenzyl)-4 -chloro-3-ethyl-1-methylpyrazole-5-carboxamide (Compound No. 6) with m.p. 73°–74° C.

$^1$H-NMR (CDCl$_3$): δ at 1.0 (t, 3H); 1.3 (t, 3H); 1.45–1.95 (m, 4H); 2.7 (q, 2H); 4.2 (s, 3H); 4.3 (t, 2H); 4.8 (d, 2H); 7.25 (bt, 1H).

N-(4-n-butoxy-2,3,5,6-tetrafluorobenzyl)-4 -chloro-1,3-dimethylpyrazole-5-carboxamide (Compound No. 7) with m.p. 71°–72° C.

$^1$H-NMR (CDCl$_3$): δ at 1.0 (t, 3H); 1.4–1.9 (m, 4H); 2.25 (s, 3H); 4.15 (s, 3H); 4.3 (t, 2H); 4.75 (d, 2H); 7.25 (bt, 1H).

N-(4-cyclopentoxy-2,3,5,6-tetrafluorobenzyl)-4 -chloro-3-ethyl-1-methylpyrazole-5-carboxamide (Compound No. 8) with m.p. 75°–76° C.

$^1$H-NMR (CDCl$_3$): δ at 1.2 (t, 3H); 1.5–2.0 (m, 8H); 2.6 (q, 2H); 4.1 (s, 3H); 4.7 (d, 2H); 4.95 (m, 1H); 7.25 (bt, 1H).

N-(4-cyclopentoxy-2,3,5,6-tetrafluorobenzyl)-4 -chloro-1,3-dimethylpyrazole-5-carboxamide (Compound No. 9) with m.p. 86°–87° C.

$^1$H-NMR (CDCl$_3$): δ at 1.5–2.0 (m, 8H); 2.2 (s, 3H); 4.1 (s, 3H); 4.7 (d, 2H); 4.95 (m, 1H); 7.2 (bt, 1H).

N-[4-(2,2,2-trifluoroethoxy)-2,3,5,6 -tetrafluorobenzyl]-4-chloro-3-ethyl-1 -methylpyrazole- 5-carboxamide (Compound No. 10) with m.p. 109°–110° C.

$^1$H-NMR (CDCl$_3$): δ at 1.2 (t, 3H); 2.6 (q, 2H); 4.1 (s, 3H); 4.5 (q, 2H); 4.7 (d, 2H); 7.2 (bt, 1H).

N-[4-(2,2,2-trifluoroethoxy)-2,3,5,6 -tetrafluorobenzyl]-4-chloro-1,3-dimethylpyrazole-5 -carboxamide (Compound No. 11) with m.p. 113°–114° C.

$^1$H-NMR (CDCl$_3$): δ at 2.2 (s, 3H); 4.1 (s, 3H); 4.5 (q, 2H); 4.7 (d, 2H); 7.2 (bt, 1H).

N-[4-(2,2,3,3-tetrafluoropropoxy)-2,3,5,6 -tetrafluorobenzyl]-4-chloro-3-ethyl-1-methylpyrazole- 5-carboxamide (Compound No. 12) with m.p. 94°–95° C.

$^1$H-NMR (CDCl$_3$): δ at 1.2 (t, 3H); 2.6 (q, 2H); 4.1 (s, 3H); 4.55 (t, 2H); 4.7 (d, 2H); 5.75–6.4 (tt, 1H); 7.2 (bt, 1H).

N-[4-(2,2,3,3,4,4,5,5-octafluoropentoxy)-2,3,5,6 -tetrafluorobenzyl]-4-chloro-3-ethyl-1-methylpyrazole- 5-carboxamide (Compound No. 13) with m.p. 62°–63° C.

$^1$H-NMR (CDCl$_3$): δ at 1.2 (t, 3H); 2.6 (q, 2H); 4.1 (s, 3H); 4.6 (t, 2H); 4.7 (d, 2H); 5.75–6.4 (tt, 1H); 7.2 (bt, 1H).

N-[4-(2,2,3,3,4,4,5,5-octafluoropentoxy)-2,3,5,6 -tetrafluorobenzyl]-4-chloro-1,3-dimethylpyrazole-5 -carboxamide (Compound No. 14) with m.p. 74°–75° C.

$^1$H-NMR (CDCl$_3$): δ at 2.2 (s, 3H); 4.1 (s, 3H); 4.65 (t, 2H); 4.7 (d, 2H); 5.75–6.4 (tt, 1H); 7.2 (bt, 1H).

N-(4-isobutoxy-2,3,5,6-tetrafluorobenzyl)-4 -chloro-3-ethyl-1-methylpyrazole-carboxamide (Compound No. 15) with m.p. 84°–86° C.

$^1$H-NMR (CDCl$_3$): δ at 0.95 (d, 6H); 1.2 (t, 3H); 2.05 (m, 1H); 2.6 (q, 2H); 3.95 (d, 2H); 4.1 (s, 3H); 4.7 (d, 2H); 7.2 (bt, 1H).

N-[4-(3-methylbutoxy)-2,3,5,6-tetrafluorobenzyl]-4-chloro-3-ethyl-1-methylpyrazole-carboxamide (Compound No. 16) with m.p. 58°–60° C.

$^1$H-NMR (CDCl$_3$): δ at 0.9 (d, 6H); 1.2 (t, 3H); 1.65 (q, 2H); 1.8 (m, 1H); 2.6 (q, 2H); 4.1 (s, 3H); 4.2 (t, 2H); 4.7 (d, 2H); 7.2 (bt, 1H).

N-[4-(3-methylbutoxy)-2,3,5,6-tetrafluorobenzyl]-4-chloro-1,3-dimethylpyrazole-carboxamide (Compound No. 17) with m.p. 65°–67° C.

$^1$H-NMR (CDCl$_3$): δ at 0.9 (d, 6H); 1.65 (q, 2H); 1.8 (m, 1H); 2.2 (s, 3H); 4.1 (s, 3H); 4.2 (t, 2H); 4.7 (d, 2H); 7.2 (bt, 1H).

N-[4-(3-methylbutyl)-2,3,5,6-tetrafluorobenzyl]-4-chloro-3-ethyl-1-methylpyrazole-carboxamide (Compound No. 18) with m.p. 83°–85° C.

$^1$H-NMR (CDCl$_3$): δ at 0.9 (d, 6H); 1.2 (t, 3H); 1.5–1.7 (m, 3H); 2.5–2.74 (m, 4H); 4.1 (s, 3H); 4.7 (d, 2H); 7.2 (bt, 1H).

N-(4-n-butylthio-2,3,5,6-tetrafluorobenzyl)-4-chloro-3-ethyl-1-methylpyrazole-carboxamide (Compound No. 19) with m.p. 83°–85° C.

$^1$H-NMR (CDCl$_3$): δ at 0.85 (t, 3H); 1.2 (t, 3H); 1.3–1.6 (m, 4H); 2.6 (q, 2H); 2.9 (t, 2H); 4.1 (s, 3H); 4.75 (d, 2H); 7.25 (bt, 1H).

N-(4-tert.butyl-2,3,5,6-tetrafluorobenzyl)-4-chloro-3-ethyl-1-methylpyrazole-carboxamide (Compound No. 20).

$^1$H-NMR (CDCl$_3$): δ at 1.2 (t, 3H); 1.45 (t, 9H); 2.6 (q, 2H); 4.1 (s, 3H); 4.7 (d, 2H); 7.2 (bt, 1H).

N-(4-n-pentoxy-2,3,5,6-tetrafluorobenzyl)-4-chloro-3-ethyl-1-methylpyrazole-carboxamide (Compound No. 21) with m.p. 57°–59° C.

$^1$H-NMR (CDCl$_3$): δ at 0.9 (t, 3H); 1.2 (t, 3H); 1.25–1.5 (m, 4H); 1.6–1.85 (m, 2H); 2.6 (q, 2H); 4.1 (s, 3H); 4.2 (t, 2H); 4.7 (d, 2H); 7.2 (bt, 1H).

N-[4-(4-methylpentoxy)-2,3,5,6-tetrafluorobenzyl]-4-chloro-3-ethyl-1-methylpyrazole-carboxamide (Compound No. 22) with m.p. 50°–51° C.

$^1$H-NMR (CDCl$_3$): δ at 0.9 (d, 6H); 1.2 (t, 3H); 1.2–1.4 (m, 2H); 1.55 (m, 1H); 1.6–1.8 (m, 2H); 2.6 (q, 2H); 4.1 (s, 3H); 4.2 (t, 2H); 4.7 (d, 2H); 7.2 (bt, 1H).

N-[4-(4-methylpentyl)-2,3,5,6-tetrafluorobenzyl]-4-chloro-3-ethyl-1-methylpyrazole-carboxamide (Compound No. 23) with m.p. 85°–87° C.

$^1$H-NMR (CDCl$_3$): δ at 0.85 (d, 6H); 1.2 (t, 3H); 1.2 (m, 2H); 1.55 (m, 3H); 2.6 (q, 2H); 2.7 (m, 2H); 4.1 (s, 3H); 4.7 (d, 2H); 7.2 (bt, 1H).

N-[4-(3,3-dimethylbutoxy)-2,3,5,6-tetrafluorobenzyl]-4-chloro-3-ethyl-1-methylpyrazole-carboxamide (Compound No. 24) with m.p. 57°–59° C.

$^1$H-NMR (CDCl$_3$): δ at 0.95 (s, 9H); 1.2 (t, 3H); 1.7 (t, 2H); 2.6 (q, 2H); 4.1 (s, 3H); 4.7 (d, 2H); 7.2 (bt, 1H).

N-[4-(3-methylbutylthio)-2,3,5,6-tetrafluorobenzyl]-4-chloro-3-ethyl-1-methylpyrazole-carboxamide (Compound No. 25) with m.p. 68°–71° C.

$^1$H-NMR (CDCl$_3$): δ at 0.85 (d, 6H); 1.2 (t, 3H); 1.6 (q, 2H); 1.75 (m, 1H); 2.6 (q, 2H); 2.9 (t, 2H); 4.1 (s, 3H); 4.7 (d, 2H); 7.2 (bt, 1H).

N-(4-n-pentylthio-2,3,5,6-tetrafluorobenzyl)-4-chloro-3-ethyl-1-methylpyrazole-carboxamide (Compound No. 26) with m.p. 67°–69° C.

$^1$H-NMR (CDCl$_3$): δ at 0.85 (t, 3H); 1.2 (t, 3H); 1.2–1.45 (m, 4H); 1.55–1.8 (m, 2H); 2.6 (q, 2H); 2.9 (t, 2H); 4.1 (s, 3H); 4.7 (d, 2H); 7.2 (bt, 1H).

N-Methyl-N-(4-n-pentoxy-2,3,5,6-tertafluorobenzyl)-4-chloro-3-ethyl-1-methylpyrazole-carboxamide (Compound No. 27).

$^1$H-NMR (CDCl$_3$): δ at 0.9 (t, 3H); 1.2 (t, 3H); 1.25–1.5 (m, 4H); 1.6–1.85 (m, 2H); 2.6 (q, 2H); 2.95 (s, 3H); 4.1 (s, 3H); 4.2 (t, 2H); 4.7 (s, 2H).

N-(4-tert.butyl-2,3,5,6-tetrafluorobenzyl)-2,6-dimethyl-2,4,5,6-tetrahydrocyclopentapyrazole-3-carboxamide (Compound No. 28).

$^1$H-NMR (CDCl$_3$): δ at 1.2 (d, 3H); 1.45 (t, 9H); 2.0 (m, 1H); 2.6 (m, 3H); 3.1 (m, 1H); 4.1 (s, 3H); 4.7 (d, 2H); 7.2 (bt, 1H).

N-[4-(N'-methyl-n-butylamino)-2,3,5,6-tetrafluorobenzyl]-4-chloro-3-ethyl-1-methylpyrazole-carboxamide (Compound No. 29) with m.p. 75°–77° C.

$^1$H-NMR (CDCl$_3$): δ at 0.9 (t, 3H); 1.2 (t, 3H); 1.25 (m, 2H); 1.5 (m, 2H); 2.6 (q, 2H); 2.9 (s, 3H); 3.1 (bt, 2H); 4.1 (s, 3H); 4.7 (d, 2H); 7.2 (bt, 1H).

N-[4-(N'-methyl-n-pentylamino)-2,3,5,6-tetrafluorobenzyl]-4-chloro-3-ethyl-1-methylpyrazole-carboxamide (Compound No. 30) with m.p. 70°–72° C.

$^1$H-NMR (CDCl$_3$): δ at 0.85 (t, 3H); 1.2 (t, 3H); 1.25 (m, 4H); 1.5 (m, 2H); 2.6 (q, 2H); 2.9 (t, 3H); 3.1 (bt, 2H); 4.1 (s, 3H); 4.7 (d, 2H); 7.1 (bt, 1H).

N-(4-n-pentylamino-2,3,5,6-tetrafluorobenzyl)-4-chloro-3-ethyl-1-methylpyrazole-carboxamide (Compound No. 31) with m.p. 101°–103° C.

$^1$H-NMR (CDCl$_3$): δ at 0.9 (t, 3H); 1.2 (t, 3H); 1.3 (m, 4H); 1.6 (m, 2H); 2.6 (q, 2H); 3.35 (m, 2H); 3.8 (m, 1H); 4.1 (s, 3H); 4.65 (d, 2H); 7.1 (bt, 1H).

N-(4-isobutoxymethyl-2,3,5,6-tetrafluorobenzyl)-4-chloro-3-ethyl-1-methylpyrazole-carboxamide (Compound No. 32).

$^1$H-NMR (CDCl$_3$): δ at 0.9 (d, 6H); 1.2 (t, 3H); 2.0 (m, 1H); 2.6 (q, 2H); 3.6 (d, 2H); 4.1 (s, 3H); 4.7 (d, 2H); 4.8 (bs, 2H); 7.2 (bt, 1H).

N-[4-(3-methylbutoxy)-3,5-dichlorobenzyl]-4-chloro-3-ethyl-1-methylpyrazole-carboxamide (Compound No. 33) with m.p. 85°–87° C.

$^1$H-NMR (CDCl$_3$): δ at 0.95 (d, 6H); 1.2 (t, 3H); 1.7 (q, 2H); 1.9 (m, 1H); 2.6 (q, 2H); 4.0 (t, 2H); 4.1 (s, 3H); 4.55 (d, 2H); 7.1 (bt, 1H); 7.25 (s, 2H).

N-[4-(4-methylpentoxy)-3,5-dichlorobenzyl]-4-chloro-3-ethyl-1-methylpyrazole-carboxamide (Compound No. 34) with m.p. 83°–85° C.

$^1$H-NMR (CDCl$_3$): δ at 0.9 (d, 6H); 1.25 (t, 3H); 1.35–1.85 (m, 5H); 2.6 (q, 2H); 4.0 (t, 2H); 4.1 (s, 3H); 4.55 (d, 2H); 7.1 (bt, 1H); 7.25 (s, 2H).

N-[4-(3,3-dimethylbutoxy)-3,5-dichlorobenzyl]-4-chloro-3-ethyl-1-methylpyrazole-carboxamide (Compound No. 35) with m.p. 101°–103° C.

$^1$H-NMR (CDCl$_3$): δ at 0.95 (s, 9H); 1.25 (t, 3H); 1.8 (t, 2H); 2.65 (q, 2H); 4.0 (t, 2H); 4.15 (s, 3H); 4.55 (d, 2H); 7.1 (bt, 1H); 7.25 (s, 2H).

EXAMPLE 4

Determination of the insecticidal and acaricidal activity.
(a) Acaricidal activity against adults of *Tetranychus urticae* (T. U.; Tetranychidae)

Disks obtained from bean leaves are infested with adult females of *Tetranychus urticae* and are subsequently dipped in a dispersion of the product to be tested in water-acetone at 10% by volume of acetone, also containing Tween 20 (0.05%).

The percent mortality rate is determined 48 hours after treatment, by comparison with the percent mortality rate of mite pests on disks only sprayed with an aqueous solution of 10% acetone (control).

The results from the determinations carried out at the dosage rates of 10 and 1 ppm are reported in Table 1, in which the following evaluation marks have been adopted:

5=100% mortality
4=91–99% mortality
3=61–90% mortality
2=31–60% mortality
1=1–30% mortality
0=0% mortality In Table 1, results are also reported which were obtained with the following reference compounds:

CRA, corresponding to N-(4-n-propylaminobenzyl)-4-chloro-3-ethyl-1-methylpyrazole-carboxamide (Compound No. 134 of European patent application No. 289,879);

CRB, corresponding to N-(4-n-butoxybenzyl)-4 -chloro-3-ethyl-1-methylpyrazole-carboxamide (Compound No. 130 of European patent application No. 289,879);

CRC, corresponding to N-(4-tert.-butylbenzyl)-4 -chloro-3-ethyl-1-methylpyrazole-carboxamide (Compound No. 51 of European patent application No. 289,879).

(b) Insecticidal activity against adults of *Macrosiphum euphorbiae* (M. E.; aphids).

Potato seedlings are infested with adult females of *Macrosiphum euphorbiae* and some hours later, are sprayed with a dispersion of the product to be tested and, in water-acetone at 10% by volume of acetone, also containing Tween 20 (0.05%)

The percent mortality rate is determined 24 hours after treatment, by comparison to the percent mortality rate of aphids infesting seedlings only treated with a water-acetone solution (at 10% by volume of acetone).

The results from the determinations carried out at the dosage rate 1 ppm are reported in Table 2, in which the following evaluation marks have been adopted:

5=100% mortality
4=91–99% mortality
3=61–90% mortality
2=31–60% mortality
1=1–30% mortality
0=0% mortality In Table 2 the results are also reported which were obtained with the following reference compound:

CRC, corresponding to N-(4-tert.-butylbenzyl)-4 -chloro-3-ethyl-1-methylpyrazole-carboxamide (Compound No. 51 of European patent application No. 289,879).

(c) Insecticidal activity against larvae of *Leptinotarsa decemlineata* (L. D.; Coleopterans).

Potato seedlings are infested with 10 5-day-old larvae of *Leptinotarsa decemlineata* and are subsequently dipped into a dispersion of the product to be tested in water-acetone at 10% by volume of acetone, also containing Tween 20 (0,005%).

The percent mortality rate is determined 48 hours after treatment, by comparison to the percent mortality rate of larvae infesting seedlings only sprayed with a 10% aqueous solution of acetone (control).

The results from the determinations carried out at the dosage rate 10 ppm are reported in Table 2, in which the following evaluation marks have been adopted:

5=100% mortality
4=91–99% mortality
3=61–90% mortality
2=31–60% mortality
1=1–30% mortality
0=0% mortality In Table 2 the results were also reported which were obtained with the following reference compound:

CRC, corresponding to N-(4-tert.-butylbenzyl)-4 -chloro-3-ethyl-1-methylpyrazole-carboxamide (Compound No. 51 of European patent application No. 289,879).

TABLE 1

Acaricidal activity against adults of *Tetranychus urticae* (T.U.).

| Compound No. | T.U. Adults 10 ppm–1 ppm |
|---|---|
| 3 | 5–3 |
| 6 | 5–1 |
| 13 | 5–5 |
| 14 | 5–4 |
| 15 | 5–2 |
| 16 | 5–3 |
| 20 | 5–4 |
| 21 | 5–4 |
| 22 | 5–4 |
| 23 | 5–4 |
| 24 | 5–4 |
| 25 | 5–4 |
| 30 | 5–4 |
| 31 | 5–2 |
| 33 | 5–4 |
| 34 | 5–4 |
| 35 | 5–4 |
| CRA | 0–0 |
| CRB | 1–0 |
| CRC | 5–1 |

TABLE 2

Insecticidal activity against adults of *Macrosiphum euphorbiae* (M.E) and larvae of *Leptinotarsa decemlineata* (L.D.).

| Compound No. | M.E. Adults 1 ppm | L.D. larvae 10 ppm |
|---|---|---|
| 3 | 5 | 5 |
| 6 | 5 | 5 |
| 15 | 5 | 5 |
| 16 | 5 | 5 |
| 21 | 5 | 5 |
| 22 | 5 | 5 |
| 23 | 5 | 5 |
| 24 | 5 | 5 |
| 25 | 5 | 5 |
| 30 | 4 | 5 |
| 31 | 4 | 5 |
| 33 | 4 | 5 |
| 34 | 4 | 5 |
| 35 | 4 | 5 |
| CRC | 2 | 1 |

We claim:

1. Amides of pyrazole carboxy acids having the general formula (I):

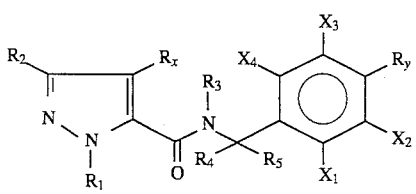

(I)

wherein:

$R_1$ and $R_2$ represent, each independently, a linear or branched $C_1$–$C_4$ alkyl radical;

$R_x$ represents a hydrogen atom, a halogen atom, a linear or branched $C_1$–$C_4$ alkyl or haloalkyl radical, a $C_1$–$C_2$ alkoxy or haloalkoxy radical; or when $R_2$ and $R_x$ are taken jointly, they represent a moiety

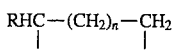

in which R represents a hydrogen atom or a $C_1$–$C_3$ alkyl radical and n is an integer of from 1 to 2;

$R_3$, $R_4$ and $R_5$ represent, each independently, a hydrogen atom or a linear or branched $C_1$–$C_4$ alkyl radical;

$X_1$, $X_2$, $X_3$ and $X_4$ represent, each independently, a halogen atom; or, when at least two from $X_1$ to $X_4$ represent halogen atoms, a hydrogen atom;

$R_y$ represents a halogen atom, a linear or branched $C_1$–$C_8$ alkyl or haloalkyl radical, a linear or branched $C_1$–$C_8$ alkoxy or haloalkoxy radical, a linear or branched $C_3$–$C_8$ alkoxy alkoxy radical, a $C_3$–$C_8$ cycloalkoxy radical, a $C_4$–$C_8$ cycloalkylalkoxy radical, a $C_1$–$C_8$ alkylthio radical, a trimethylsilyl radical; a linear or branched $C_3$–$C_8$ alkoxyalkyl or haloalkoxyalkyl radical; a $C_2$–$C_8$ alkylamino or dialkylamino radical; or when all of $X_1$–$X_4$ are halogen atoms, $R_y$ represents a phenoxy or a phenylthio radical, with said radicals being optionally substituted with halogen atoms, linear or branched alkyl or haloalkyl $C_1$–$C_4$ radicals, linear or branched $C_1$–$C_4$ alkoxy or haloalkoxy radicals.

2. Acaricides and insecticides according to claim 1, in which $X_1$, $X_2$, $X_3$ and $X_4$ represent a fluorine atom.

3. Acaricide and insecticide according to claim 1, which is N-(4-n-pentyl-2,3,5,6-tetrafluorobenzyl)-4-chloro-3-ethyl-1-methylpyrazole-carboxamide.

4. Acaricide and insecticide according to claim 1, which is N-[4-(2,2,3,3,4,4,5,5-octafluoropentoxy)-2,3,5,6-tetrafluorobenzyl]-4-chloro-3-ethyl-1-methylpyrazole-carboxamide.

5. Acaricide and insecticide according to claim 1, which is N-[4-(2,2,3,3,4,4,5,5-octafluoropentoxy)-2,3,5,6-tetrafluorobenzyl]-4-chloro-1,3-dimethylpyrazole-carboxamide.

6. Acaricide and insecticide according to claim 1, which is N-[4-(3-methylbutoxy)-2,3,5,6-tetrafluorobenzyl]-4-chloro-3-ethyl-1-methylpyrazole-carboxamide.

7. Acaricide and insecticide according to claim 1, which is N-(4-tert.-butyl-2,3,5,6-tetrafluorobenzyl)-4-chloro-3-ethyl-1-methylpyrazole-carboxamide.

8. Acaricide and insecticide according to claim 1, which is N-(4-pentoxy-2,3,5,6-tetrafluorobenzyl)-4-chloro-3-ethyl-1-methylpyrazole-carboxamide.

9. Acaricide and insecticide according to claim 1, which is N-[4-(4-methylpentoxy)-2,3,5,6-tetrafluorobenzyl]-4-chloro-3-ethyl-1-methylpyrazole-carboxamide.

10. Acaricide and insecticide according to claim 1, which is N-[4-(4-methylpentyl)-2,3,5,6-tetrafluorobenzyl]-4-chloro-3-ethyl-1-methylpyrazole-carboxamide.

11. Acaricide and insecticide according to claim 1, which is N-[4-(3,3-dimethylbutoxy)-2,3,5,6-tetrafluorobenzyl]-4-chloro-3-ethyl-1-methylpyrazole-carboxamide.

12. Acaricide and insecticide according to claim 1, which is N-[4-(3-methylbutylthio)-2,3,5,6-tetrafluorobenzyl]-4-chloro-3-ethyl-1-methylpyrazole-carboxamide.

13. Acaricide and insecticide according to claim 1, which is N-[4-(N'-methyl-n-pentylamino)-2,3,5,6-tetrafluorobenzyl]-4-chloro-3-ethyl-1-methylpyrazole-carboxamide.

14. Acaricide and insecticide according to claim 1, which is N-[4-(3-methylbutoxy)-3,5-dichlorobenzyl]-4-chloro-3-ethyl-1-methylpyrazole-carboxamide.

15. Acaricide and insecticide according to claim 1, which is N-[4-(4-methylpentoxy)-3,5-dichlorobenzyl]-4-chloro-3-ethyl-1-methylpyrazole-carboxamide.

16. Acaricide and insecticide according to claim 1, which is N-[4-(3,3-dimethylbutoxy)-3,5-dichlorobenzyl]-4-chloro-3-ethyl-1-methylpyrazole-carboxamide.

17. Compositions having acaricidal and insecticidal activity, containing one or more compounds according to claim 1, either alone or in presence of solid carriers, liquid diluents, surfactants or other active principles.

18. Compositions having acaricidal and insecticidal activity according to claim 17, in which the concentration of active substances is comprised within the range of from 1% to 90%.

\* \* \* \* \*